US011116651B2

(12) United States Patent
Xue et al.

(10) Patent No.: US 11,116,651 B2
(45) Date of Patent: Sep. 14, 2021

(54) VASCULAR STENT DELIVERY SYSTEM AND TUBING ASSEMBLY THEREOF

(71) Applicant: SUZHOU INNOMED MEDICAL DEVICE CO., LTD, Jiangsu (CN)

(72) Inventors: Guanhua Xue, Suzhou (CN); Pengchong Qiu, Suzhou (CN); Jichang Wei, Suzhou (CN); Hui Li, Suzhou (CN)

(73) Assignee: SUZHOU INNOMED MEDICAL DEVICE CO., LTD, Suzhou (CN)

( * ) Notice: Subject to any disclaimer, the term of this patent is extended or adjusted under 35 U.S.C. 154(b) by 320 days.

(21) Appl. No.: 16/093,619

(22) PCT Filed: Apr. 12, 2017

(86) PCT No.: PCT/CN2017/080216
§ 371 (c)(1),
(2) Date: Oct. 12, 2018

(87) PCT Pub. No.: WO2017/177915
PCT Pub. Date: Oct. 19, 2017

(65) Prior Publication Data
US 2019/0125563 A1    May 2, 2019

(30) Foreign Application Priority Data

Apr. 12, 2016 (CN) .......... 201610224524.8
Apr. 12, 2016 (CN) .......... 201610224595.8
(Continued)

(51) Int. Cl.
*A61F 2/966* (2013.01)
*A61F 2/962* (2013.01)
(Continued)

(52) U.S. Cl.
CPC .......... *A61F 2/966* (2013.01); *A61F 2/95* (2013.01); *A61F 2/962* (2013.01);
(Continued)

(58) Field of Classification Search
CPC ........ A61F 2210/0014; A61F 2250/007; A61F 2/95; A61F 2/9517; A61F 2/962; A61F 2/966
See application file for complete search history.

(56) References Cited

U.S. PATENT DOCUMENTS 8,043,301 B2   10/2011   Adams et al.
9,375,335 B2    6/2016   Bialas et al.
(Continued)

FOREIGN PATENT DOCUMENTS

CN    102038565 A    5/2011
CN    102038565 A    5/2011
(Continued)

OTHER PUBLICATIONS

First Search for Chinese Application No. 201610224890.3 dated Feb. 27, 2018.
(Continued)

*Primary Examiner* — Mohamed G Gabr
(74) *Attorney, Agent, or Firm* — Jenkins, Wilson, Taylor & Hunt, PA

(57) ABSTRACT

A vascular stent conveying system includes a housing, an outer cannula, a cleaning tube, an inner cannula, and a driving assembly. The outer cannula is located outside the housing and is connected to a first end of the housing. The cleaning tube is connected to a second end of the housing, a first end of the cleaning tube is located in the housing, and a second end of the cleaning tube extends out of the housing. A part of the inner cannula is located in the housing, a first end of the inner cannula extends into the outer cannula, and
(Continued)

a second end of the inner cannula extends from the first end of the cleaning tube to a tube chamber of the cleaning tube. A part of the driving assembly is located in the housing, and operably engaged with a part of the inner cannula located in the housing.

16 Claims, 17 Drawing Sheets

(30) Foreign Application Priority Data

| Apr. 12, 2016 | (CN) | 201610224686.1 |
|---|---|---|
| Apr. 12, 2016 | (CN) | 201610224890.3 |
| Apr. 12, 2016 | (CN) | 201620301609.7 |
| Apr. 12, 2016 | (CN) | 201620301791.6 |
| Apr. 12, 2016 | (CN) | 201620301792.0 |
| Apr. 12, 2016 | (CN) | 201620301833.6 |

(51) Int. Cl.
*A61F 2/95* (2013.01)
*A61M 25/00* (2006.01)

(52) U.S. Cl.
CPC .... *A61F 2210/0014* (2013.01); *A61M 25/005* (2013.01); *A61M 25/0012* (2013.01); *A61M 2025/0019* (2013.01); *A61M 2025/0047* (2013.01)

(56) References Cited

U.S. PATENT DOCUMENTS

| 9,662,238 | B2 | 5/2017 | Dwork et al. |
| 9,889,029 | B2 | 2/2018 | Li et al. |
| 10,292,848 | B2 | 5/2019 | Gong et al. |
| 2004/0181239 | A1 | 9/2004 | Dorn |
| 2007/0156223 | A1 | 7/2007 | Vaughan |
| 2008/0097572 | A1 | 4/2008 | Sheldon et al. |
| 2013/0304179 | A1* | 11/2013 | Bialas ............... A61M 25/09 623/1.11 |
| 2014/0303722 | A1* | 10/2014 | Alkhatib ............ A61F 2/013 623/2.11 |

FOREIGN PATENT DOCUMENTS

| CN | 102283728 A | 2/2012 |
| CN | 102488577 A | 6/2012 |
| CN | 102985037 A | 3/2013 |
| CN | 103431926 A | 12/2013 |
| CN | 203408335 U | 1/2014 |
| CN | 103655004 A | 3/2014 |
| CN | 203647541 U | 6/2014 |
| CN | 103961194 A | 8/2014 |
| CN | 104168860 A | 11/2014 |
| CN | 104546243 A | 4/2015 |
| CN | 104546246 A | 4/2015 |
| CN | 104758098 A | 7/2015 |
| CN | 204428220 U | 7/2015 |
| CN | 205698141 U | 11/2016 |
| CN | 205698142 U | 11/2016 |
| CN | 205698143 U | 11/2016 |
| CN | 107280829 B | 10/2018 |
| CN | 107280828 B | 2/2019 |
| CN | 107280830 B | 2/2019 |
| CN | 107280831 B | 2/2019 |
| VN | 205698144 U | 11/2016 |
| WO | WO 2014/142808 A1 | 9/2014 |

OTHER PUBLICATIONS

First Search for Chinese Applcation No. 201610224524.8 dated Mar. 8, 2018.
First Search for Chinese Applcation No. 201610224595.8 dated Mar. 8, 2018.
First Search for Chinese Applcation No. 201610224686.1 dated Mar. 14, 2018.
International Search Report and Written Opinion for Application No. PCT/CN2017/080216 dated Jun. 29, 2019.
European Search Report for Application No. 17781891.1 dated Mar. 4, 2020.

* cited by examiner

VASCULAR STENT DELIVERY SYSTEM AND TUBING ASSEMBLY THEREOF

CROSS REFERENCE TO RELATED APPLICATIONS

This is a National Stage Application, filed under 35 U.S.C. 371, of International Patent Application No. PCT/CN2017/080216, filed on Apr. 12, 2017, which claims the benefit of, and priority to, Chinese Patent Application Serial Nos. 201610224890.3, 201620301833.6, 201610224524.8, 201620301792.0, 201610224686.1, 201620301609.7, 201610224595.8 and 201620301791.6 filed on Apr. 12, 2016, the entire disclosures of which are hereby incorporated by reference in their entireties.

TECHNICAL FIELD

This invention is categorized as a medical device and is intended to be a vascular stent delivery system. This report presents in detail the tubing system associated with this invention along with a manufacturing methodology.

BACKGROUND

Stents therapy, also known as minimally invasive surgery using stents, has emerged to become a popular method for treating peripheral vascular disease, because of its small incision size. This operation reduces complications and improves overall safety profile.

Stents therapy requires a delivery system to implant vascular stents into the body. In the prior arts, the delivery system is comprised of a tubing assembly, a driving assembly, and a handle. The tubing assembly is comprised of an outer and inner cannula between which the vascular stent lies. These portions are hollow for the guidewires to pass through. The driving assembly mobilizes the inner cannula longitudinally in order to deploy the stent. The outer cannula is fixed to the housing and the driving assembly is operably engaged with the inner cannula.

During the surgery, the operator uses the guidewire to navigate the tubing assembly to the surgery site. The driving assembly mobilizes the inner cannula axially forward to introduce the stent into the vasculature. From there, the stent unfolds to support the inner wall of the vessel.

In the prior arts, a cleaning tube is incorporated in the delivery system. This component is located within the handle housing and is in communication with the inner cannula cavity. A clean fitting can be attached to the end of the cleaning tube to clean the inner cannula and its cavity after each use. The cleaning tube typically includes a middle steel tube coupled to the driving assembly and sleeved within the inner cannula. The middle steel tube is affixed to the connection part of the housing. The inner cannula, however, will move relative to the middle steel tube, resulting in unwanted contact and subsequent scratching between the inner and middle steel tubes. This decreases the overall service life of the delivery system. A plurality of connections within the cleaning pipeline easily cause leakage of liquid at respective connection sites, resulting in liquid flowing into the driving assembly and the housing.

Within the prior arts, it is difficult for the tubing assembly to arrive at intensely curved lesion sites due to its poor flexibility. Adjusting the tubing stiffness can facilitate bending to enhance device performance. Additionally, FIG. 13 shows that the inner cannula 800 is formed integrally and rachets 900 are coupled to the inner cannula 800. Therefore, during introduction of the stent, the rachets are bent due to poor stiffness. In the prior arts, the cone tip (TIP) of the tubing assembly is directly adherent to the inner cannula with limited joint intensity, resulting in risk of accidental detachment.

SUMMARY

A vascular stent delivery system with its accompanying tubing assembly along with a manufacturing methodology is provided in this section.

The delivery system is comprised of the following: a housing, an outer cannula, a cleaning tube, an inner cannula, and a driving assembly. The outer cannula is attached to the first end of the housing via a stress dispersion assembly and extends outside the housing through an opening. The cleaning tube is affixed to the second end of the housing and extends outward through an opening at the back. An inner cannula is threaded between the outer cannula and the cleaning tube. The portion of this tube within the cleaning tube is modified to prevent it from scratching the cleaning tube cavity's inner wall. A driving assembly, a part of which is disposed within the housing and is operably engaged with a part of the inner cannula is there to move the inner cannula axially in the outer cannula and the cleaning tube. The method to manufacture this vascular stent delivery system is based on putting together the aforementioned components.

The tubing assembly of the vascular stent delivery system is made of an outer cannula, an inner cannula, and a tip having a channel passing along the length. A part of this tip is inserted into the outer cannula and attached to the inner cannula through a connection tube to facilitate movement of the tubing assembly. The inner cannula is affixed within the outer cannula and comprises of a metal braided tube. Rachets are affixed to the metal portion of the inner cannula and configured to move the stent when the inner cannula is displaced relative to the outer cannula. The present invention achieves the following advantages:

The operability of the delivery system is improved through the anti-scratching treatment between the inner and cleaning tube. This enhances the service life of the delivery system. Additionally, the integral formation of the cleaning tube, as compared with past prototypes, has a reduced risk of liquid leakage, which results in improved operability and reliability of the system.

The stress dispersion assembly is used for dispersing the stresses concentrated on the joint site between the outer cannula and the housing. The flexibility of the tube is maintained and the tube will not be easily broken off. The operability and service life of the vascular stent delivery system is effectively improved.

Since the inner cannula consists of the metal braided tube along with the metal tube, arrangement of the rachets on the metal tube enhances the overall rigidity of the rachets, and the bending rendered due to a lack of rigidity can be addressed.

The tip is attached to the inner cannula through a connection tube formed through the injection molding method. As a result, the joint intensity is enhanced for preventing the tip from accidental detachment and enhancing the reliability of the delivery system of vascular stent to lower the risk for the patient.

DETAILED DESCRIPTION

Various aspects of the invention are described below by reference to appended drawings and detailed embodiments. The drawings are not drawn to scale for the purpose of illustrating the principles of the present invention.

This report does not present various structures, materials, or operations in much detail. Moreover, features, structures, or characters as described herein can be combined in one or more embodiments by any manner. Those skilled in the art should understand that the various components described below are set forth for illustration, but not intended to limit the scope of the present invention. Also, it should be stated that the elements or members described and drawn herein could be arranged and designed in various configurations.

Example 1

Figure 1:
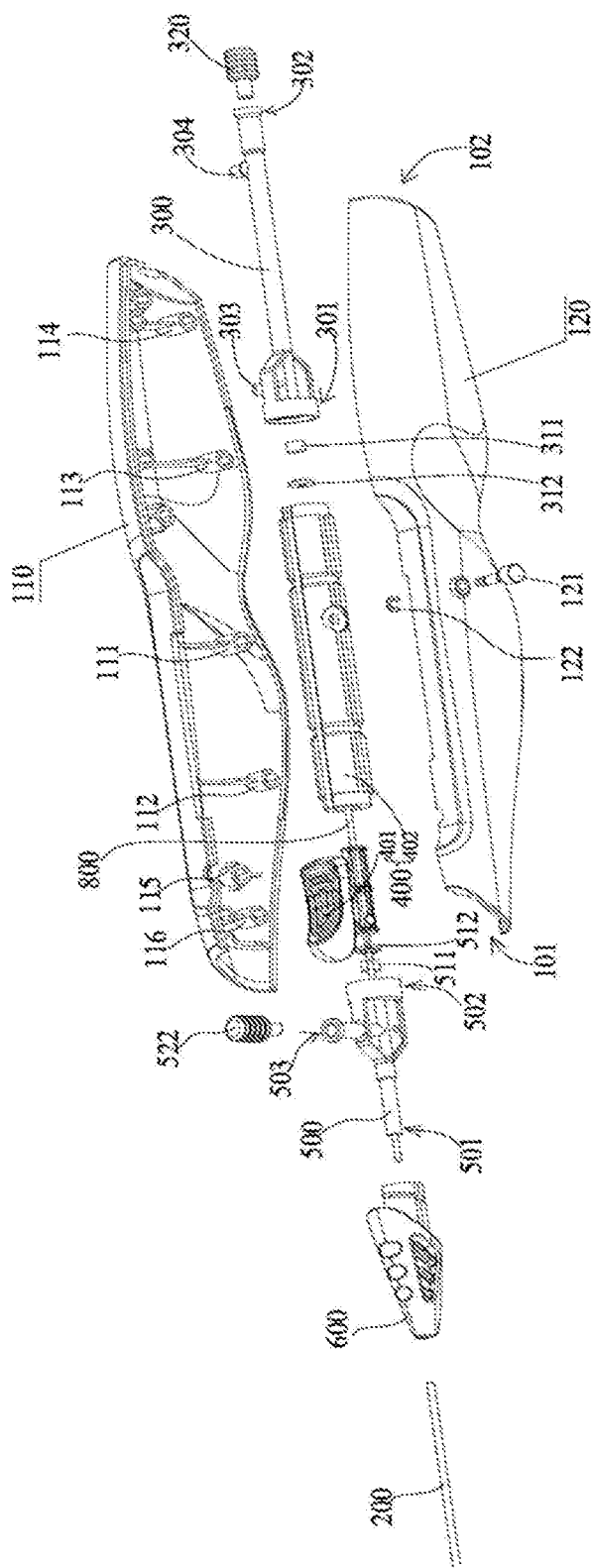
FIG. 1 is a perspective exploded view of the vascular stent delivery system.
Figure 2:
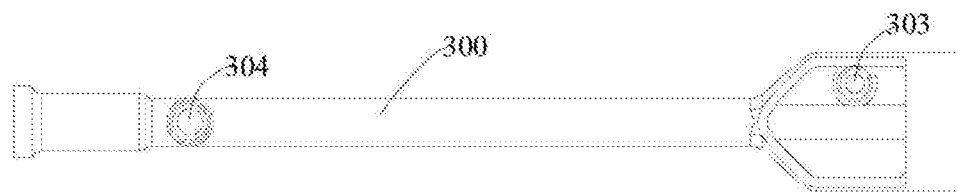
FIG. 2 is a perspective view of the cleaning tube of the vascular stent delivery system.
Figure 3:
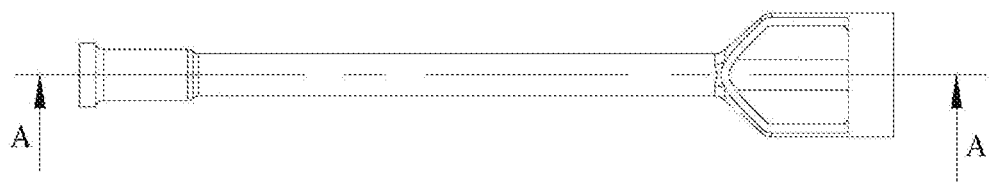
FIG. 3 is a perspective view of the cleaning tube of the vascular stent delivery system from a view different from that of FIG. 2.

FIG. 1 shows a vascular stent delivery system. This system may consist of a right half housing 110, a left half housing 120, an outer cannula 200, a cleaning tube 300, an inner cannula 800, and a driving assembly 400.

The outer cannula 200 is located outside the housing and coupled to the first end 101 of the housing. A three-way tube 500 is attached to the first end 101 of the housing by a rubber head 600 (joint member). Particularly, the outer cannula 200 passes through the rubber head 600 and extends to the first end 501 of the three-way tube 500 (the detailed structure thereof will be described as below) such that the outer cannula 200 is in communication with the three-way tube 500 and the rubber head 600 is fixed to the housing. The rubber head 600 is sandwiched in and held by the right 110 and the left half housing 120, both of which are fixed together by fitting the nut 121 with the connection feature 111 (such as screw hold). As an alternative, the rubber head 600 and the three-way tube 500 can be omitted and the outer cannula 200 can be directly fixed to the housing.

The cleaning tube 300 cleans the delivery system once the vascular stent is transported. It is an integrally formed two-way tube, also called the LUER tube, is formed by polycarbonate (PC), and coupled to the second end 102 of the housing. The first end 301 of the cleaning tube 300 is disposed within the housing and the second end 302 extends out of the housing to the outer space. In one version, the cleaning tube 300 is provided with connection features 303 and 304. Connection features 113 and 114 corresponsive to the connection features 303 and 304 are disposed on the corresponding locations on the right half housing 110. The cleaning tube 300 is fixed to the housing by embedding connection features 303 and 304 into connection features 113 and 114. As a result, the cleaning tube 300 is held by the right 110 and left half housing 120.

A part of the inner cannula 800 is contained within the housing, which can be formed from a steel tube (i.e. inner steel tube) but is not limited to this. The inner cannula 800 can be formed from other suitable materials that can be used for the vascular stent delivery system. The first end of the inner cannula 800 extends into the outer cannula 200. The inner cannula 800 is inserted into the second end 502 of the three-way tube 500. It then passes through the three-way tube 500 and extends into the cavity of the outer cannula 200. In other versions, the three-way tube 500 can be omitted. As such, the first end of the inner cannula 800 directly extends into the cavity of the outer cannula 200. The second end of the inner cannula extends into the cavity of the cleaning tube 300 from the first end 301 of the cleaning tube 300 (FIGS. 4 and 5).

A portion of the driving assembly 400 is operably engaged with the inner cannula 800 and both are affixed to the inner portion of the housing. Specifically, the driving assembly 400 consists of a thumb drive member 401 and a guide rail 402. The driving assembly 400 is connected between the first and second ends of the inner cannula. The right half housing 110 is coupled to the driving assembly 400 through the connection features 112, 115, and 116. The nut 121 passes through the hole on the left half housing 120 and holes on the clamping spring 122. The guide rail 402 extends into the screw hole 111 on the right half housing 110. The left 120 and right half housing 110 are combined together by engaging the nut 121 with the screw hole 111 such that a part of the driving assembly 400 is received in the housing and, meanwhile, a part of the thumb driving member 401 is exposed out of the housing to be used by the operator. The inner cannula 800 passes through the guide rail 402 and is engaged with a part of the thumb-driving member 401. When the thumb-driving member 401 is used, the inner cannula 800 moves along the guide rail 402 by pulling and pushing the thumb driving member 401 such that the inner cannula axially moves in the inner cavity of the outer cannula and the cleaning tube. In particular, the first end of the inner cannula moves in the outer cannula 200 such that the vascular stent moves along the outer cannula 200 and enters into the vessels. Thereafter, the vascular stent unfolds to support the inner wall of the vessel. Meanwhile, the second end of the inner cannula moves in the cleaning tube 300 with movement of the inner cannula as a whole.

Figure 4:
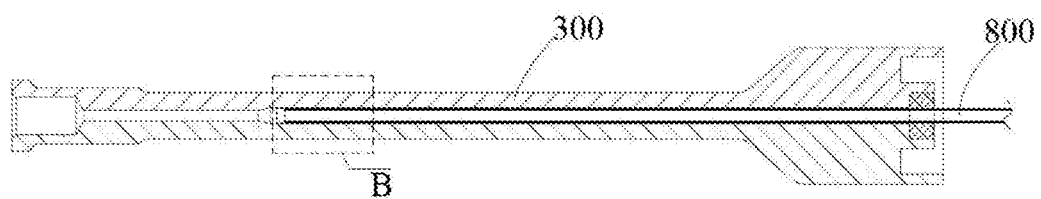
FIG. 4 is a cross-sectional view of the cleaning tube of the vascular stent delivery system along the A-A line as shown in FIG. 3. An inner cannula is inserted into the cleaning tube.
Figure 5:
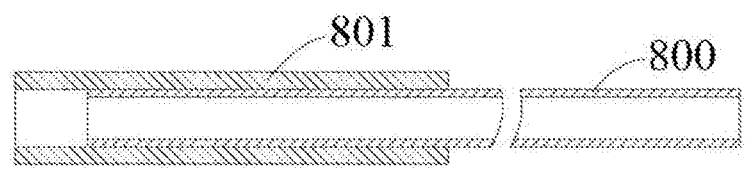
FIG. 5 is an enlarged view of B part of FIG. 4.
Figure 6:
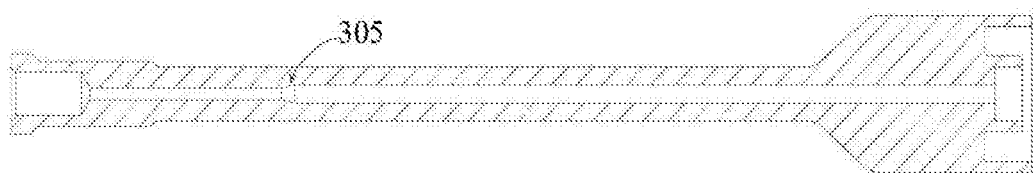
FIG. 6 is a cross-sectional view of the cleaning tube of the delivery system along the A-A line as shown in FIG. 3. An inner cannula is not inserted into the cleaning tube.

A heat shrink tube 801 is added to the inner cannula's second end 800 to prevent scratching between the inner cannula and the cleaning tube's inner wall (FIGS. 4 and 5). This tube is made of polyperfluorinated ethylene propylene (PEP) to prevent slippage. Even if there is an assembly error, the relative movement driven by pushing and pulling the inner cannula will not result in scratching of the cleaning tube's inner wall. The PEP has a smooth surface from the reduced frictional resistance of PC. The distal end of the inner cannula's second end is formed as a fillet to reduce frictional resistance between it and the cleaning tube wall. This protects the wall during use.

The cleaning tube 300 is a part of the LUER tube and is an integrally formed two-way tube made of PC material. This ensures that the cleaning tube is leak proof, which enhances the overall operability and reliability of the system. The integral production method of this part lowers its overall cost. The distal end 302 of the cleaning tube 300 has an opening and joint cap 320 for sealing the opening. During stent deployment, the joint cap 320 occludes the opening to prevent body fluid (i.e. blood) from flowing out. Upon completion of the vascular stent transport, the joint cap 320 is opened so that the cleaning fluid can be added to the delivery system.

A fitting 305 for the guide wire to pass through is located within the cleaning tube 300 between the first and second ends. The cavity of the cleaning tube at the fitting has a tapered inner diameter correlating with its gradient design. This feature is present to facilitate guidewire movement within.

The three-way tube 500 is used for cleaning the front end, or the part adjacent to the outer cannula, of the vascular stent delivery system. The three-way tube can be a LUER three-way tube for the vascular stent delivery system. FIG. 1 shows the three-way tube 500 is connected at the first end 101 of the housing, which has a first end 501 extending out from the housing to the outer space. A second end 501 is contained within the housing and is in communication with the first end 501. A third end 503 is disposed between the first 501 and second 502 ends.

The first end 501 of the three-way tube 500 is in communication with the outer cannula 200. This end 501 is coupled to and in communication with the outer cannula 200 via the rubber head 600. The first end of the inner cannula is inserted into the second end 502 of the three-way tube and passes through the three-way tube 500 to extend out from the first end 501 of the three-way tube 500 into the outer cannula 200. The distal end of the third end 503 of the three-way end 500 has an opening and a joint cap 522 for closing this opening. During transportation of the vascular stent, the opening is closed by the joint cap 522 to prevent body fluid, such as blood, from flowing out. Upon completing the vascular stent transportation, the joint cap 522 is opened through which the cleaning fluid is added to clean the front part of the vascular stent delivery system.

Figure 7:
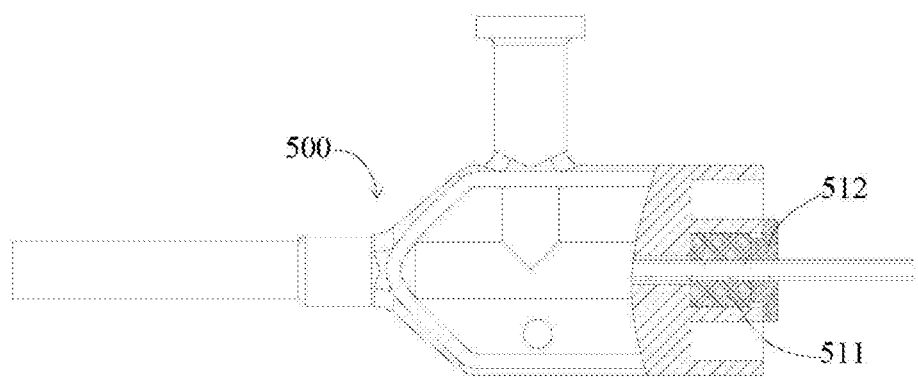
FIG. 7 is a topical Three-way pipe cross-sectional view.
Figure 8:
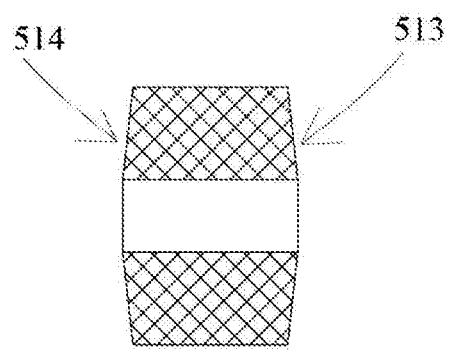
FIG. 8 is a cross-sectional view of the O-shaped ring for the vascular stent delivery system.

Within this embodiment, the sealing assemblies (311, 312, 511, 512) are disposed at the distal ends of the first end 301 of the cleaning tube 300 and the second end 502 of the three-way tube 500. The inner cannula can pass through the sealing assemblies. For instance, the sealing assemblies have channels through which the inner cannula passes. Particularly, as shown in FIGS. 1 and 4, a sealing assembly comprising an O-shaped ring 311 and a cover plate 312 for fixing such O-shaped ring is disposed at the distal end of the first end 301 of the cleaning tube 300. As shown in FIGS. 1 and 7, a sealing assembly comprising an O-shaped ring 511 and a cover plate 512 for fixing such an O-shaped ring is connected at the distal portion of the second end 502 of the three-way tube 500. Either or both the O-shaped rings 311 and 511 is/are configured to have the thickness gradually decreased from the center to the edge. As shown in FIG. 8, two sides 513 and 514 of the O-shaped ring are present as a conical surface, respectively. The O-shaped ring with conical surface design cooperates with the LUER two-way and three-way tubes, and there is always a line along the circumference that exhibits interference fit with the LUER two-way or three-way tubes such that even if the inner cannula moves, the O-shaped ring with conical surface design has less axial movement than the O-shaped ring with a flat surface. In other embodiments described within, the surface for contacting the O-shaped ring with the inner cannula is coated with a lubricating layer, comprised of any one of parylene, polytetrafluoroethylene (PTFE), polyvinylpyrrolidone (PVP) and silicone oil. The lubricating layer made of parylene coating. Due to pressure differential in the body, blood backflow will occur after the interventional catheter is inserted. The O-shaped ring must exhibit interference first with the inner cannula; however, such interference fit will have influence on the delivery feel for the operator. The parylene coating combined with the O-shaped ring will lower friction due to the smoothness of the coating, and facilitate its use.

The foregoing intends for illustration of the present invention but is not limited to this. In other embodiments, the sealing assembly mentioned can be disposed at either of the first end 301 of the cleaning tube 300 or the second end 502 of the three-way tube 500. The sealing assembly as mentioned above can be merely disposed at the second end 502 of the three-way tube 500.

According to other embodiments described in this report, the anti-scratching treatment between the inner cannula and cleaning tube can effectively improve the operability and service life of the vascular stent delivery system. The methodology for manufacturing the vascular stent delivery system is described in detail below.

Manufacturing the vascular stent include providing a housing, an outer cannula, a cleaning tube, an inner cannula, and a driving assembly. The outer cannula is configured to be disposed outside the housing and attached to the first end of the housing. A cleaning tube is attached to the second end of the housing, the first end of which is disposed within the housing and the second end of which extends out from the housing to the outer space. An inner cannula, a part of which is disposed within the housing, has a first end that extends into the outer cannula and a second end that extends from the cleaning tube's first end into the cleaning tube cavity. The driving assembly is configured so that a portion of this is contained within the housing and operably engaged with the part of the inner cannula that is disposed within the housing for driving the inner cannula to axially move in the outer cannula and the cleaning tube.

The second end of the inner cannula's distal end is configured to prevent it from scratching the cleaning tube's inner wall. This configuration prevents scratching with cleaning tube's inner wall and provides a heat shrink tube through which the distal portion of the inner cannula's second end is inserted. The portion of the inner cannula's second end that makes contact with the heat shrink tube is subject to anti-slipping treatment. As an alternative, the distal part of the inner cannula's second end can be fixably coupled to the heat shrink tube.

The cleaning tube is an integrally formed two-way tube made of PC material, making it relatively leak proof to improve the operability and reliability of the system. Additionally, a fitting for the guidewire to pass there through is disposed within the cleaning tube and between the first and second end of the cleaning tube.

In some embodiments, the cleaning tube cavity at the fitting for guidewire has a gradually decreasing inner diameter, which pertains to a gradient design. This facilitates guidewire movement through the inner cavity and avoids the stairs and stuck phenomenon.

In another version, an opening is disposed at the distal end of the cleaning tube's second end and provided with a joint cap for closing the opening. During vascular stent transportation, the joint cap can close the opening to prevent blood from flowing out. Upon complete transport of the vascular stent, the joint cap can be opened and the cleaning fluid is then added to the vascular stent delivery system. This method also includes providing a three-way tube, such as the LUER tube, attached to the housing's first end and with a first end extending into the housing's outer space and a second end contained within the housing and in linear communication with the other tubing assemblies. The three-way tube's first end connects with the outer cannula and inserts into the second end to pass through the distal end into the outer cannula. The distal part of the three-way tube has an opening closed by the joint cap. As such, during transportation of the vascular stent, the opening is closed by the joint cap to prevent body fluid, such as blood, from flowing out. Upon completion of the endovascular procedure, the joint cap is opened and the cleaning fluid can be added to clean the front part of the vascular stent delivery system.

In yet another example, a sealing assembly is affixed to the end of at least one first end of the cleaning tube (i.e. two-way tube) and the second end of the three-way tube. The inner cannula can pass through the sealing assembly. Alternatively, the sealing assembly may comprise of an O-shaped ring configured to have thickness gradually decreasing from the center to the edge. For instance, the surface for contacting the O-shaped ring with the inner cannula is coated with a lubricating layer, which can be made of Parylene, Polytetrafluoroethylene (PTEE), Polyvinylpyrrolidone (PVP), and silicone oil. The vascular stent delivery system manufactured by the method described can effectively improve the overall operability and service life of the device.

Example 2

The vascular stent delivery system can include, but is not limited to, a right half housing 110, a left half housing 120, an outer cannula 200, a cleaning tube 300, an inner cannula 800, and a driving assembly 400.

The specific structure of the inner cannula 800, driving assembly 400, three-way tube 500, and cleaning tube 300 are described above. Alternatively, in other embodiments herein, the cleaning tube 300 can be omitted. For the disposable vascular stent delivery system, there is no need to clean the delivery system cleaning tube 300. Thus, such vascular stent delivery system does not comprise the cleaning tube 300. As an alternative, in other embodiments described herein, the three-way tube 500 can be omitted. For instance, for the disposable vascular stent delivery system, there is no need to use the three-way tube 500 to clean the delivery system. Therefore, such a vascular stent delivery system does not comprise the three-way tube 500. Therefore, the first end of the inner cannula 800 is directly inserted into the outer cannula 200.

The outer cannula 200 is connected outside the housing and coupled to the first end 101 through a stress dispersion assembly. This assembly may comprise, but is not limited to, a joint member 600, a stress dispersion tube 700, and a guide tube (i.e. a three-way tube 500 in this example). Particularly, the stress dispersion tube 700 passes through the joint member 600 and extends into the first end 501 of the three-way tube 500. The outer cannula 200 inserts into the stress dispersion tube and extends to the first end 501 of the three-way tube 500 such that the outer cannula 200 is in communication with the three-way tube 500 (i.e. the first end 501 of the three-way tube 500 is coupled to and in communication with the outer cannula 200 through the stress dispersion tube 700 and joint member 600). The joint member 600 is fixed to the housing and is held by the right 110 and left 120 half housing. Both of these are fixed by fitting the nut 121 with the connection feature 111.

The following is a description of the specific structure of the stress dispersion assembly.

The vascular stent delivery system's outer cannula is coupled to the housing through the stress dispersion assembly. The stress concentrated at the outer cannula joint and housing is dispersed by the stress dispersion assembly. Therefore, the flexibility of the tube is sustained and the tube will not be broken off.

Figure 9:
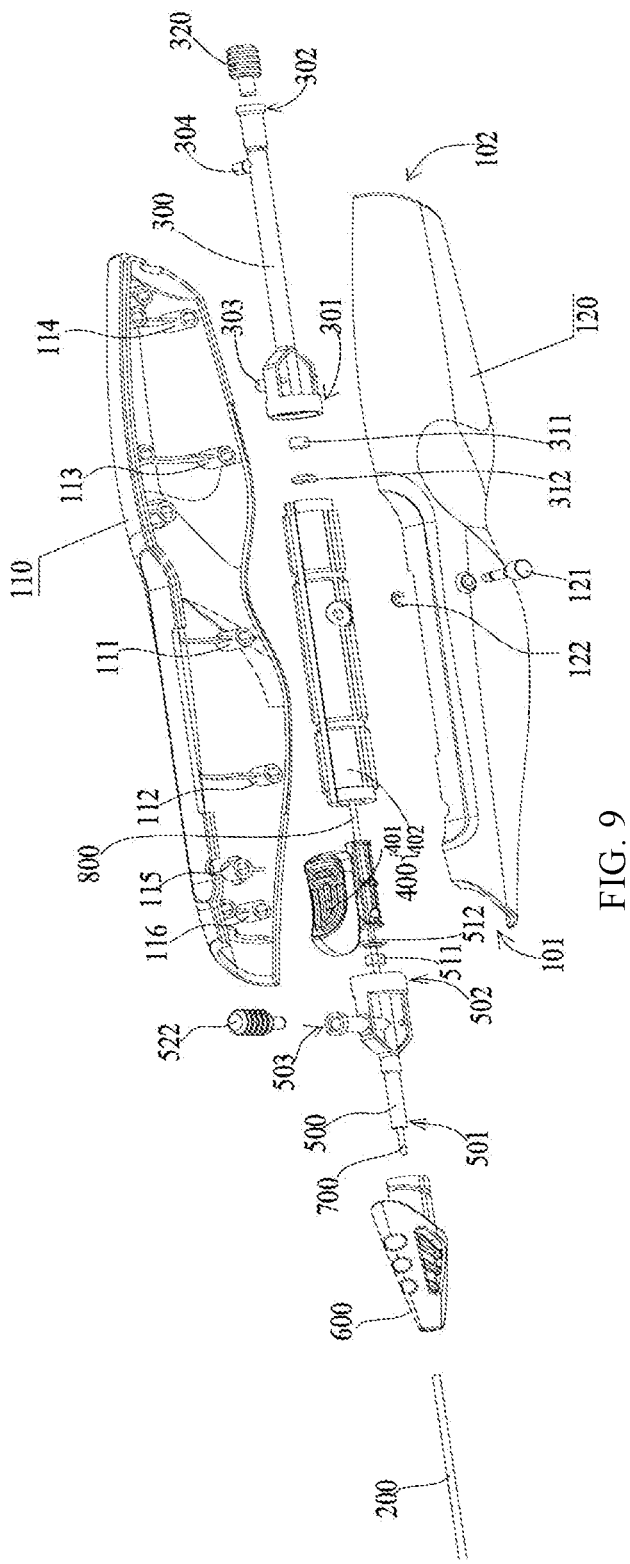
FIG. 9 is a perspective exploded view of the stress dispersion assembly.
Figure 10:
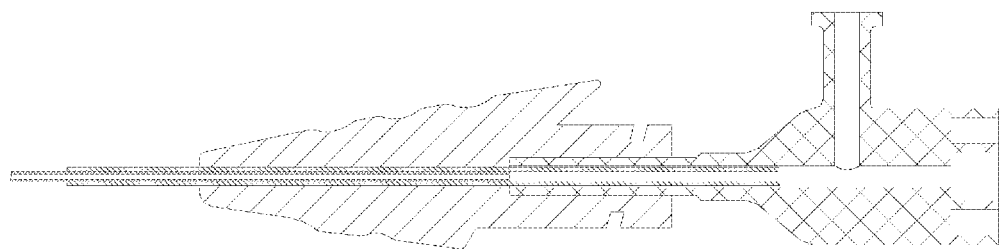
FIG. 10 is a cross-sectional view of the stress dispersion assembly.

FIGS. 9 and 10 show the stress dispersion assembly is configured to the joint member 600 and has a channel from the first end 601 to the second end 602 along the length direct (i.e. axial direction of the tube) and the second end 602 of the joint member 600 is fixably coupled to the housing. As mentioned above, a part of the guide tube (i.e. first end 501 of the three-way tube 500) extends from the second end 602 of the joint member 600 to the channel in the joint member 600. Another part of the guide tube (e.g. the second end 502 of the three-way tube 500) is disposed within the housing. A part of the stress dispersion tube 700 is disposed outside the joint member 600. Another part of the stress dispersion tube 700 extends from the first end 601 of the joint member 600 into the channel in the joint member 600 to pass through the said channel to extend into the guide tube (i.e. the first end 501 of the three-way tube 500 extends into the three-way tube 500). The outer cannula 200 inserts into the stress dispersion tube 700 and extends through the stress dispersion tube 700 into the joint member 600. The inner cannula 800 is able to pass through the guide tube and the stress dispersion tube 700 to extend into the outer cannula 200 in order to mobilize the outer cannula 200 under the driving assembly 400. This function transports the vascular stent into the body. In one embodiment, the outer cannula 200 can be a tube braided by PEBAX (block polyether acidamide resin) steel wires. The stress dispersion tube 700 can be a PA12 (polylaurylamide) tube and the joint member 600 can be a rubber head. The guide tube can be formed from ABS (i.e. terpolymer of acrylonitrile, butadiene and styrene, A represents acrylonitrile, B represents butadiene, S represents styrene) material. Alternatively, the tubes braided by PEBAX steel wires consist of three layers. The outer layer is PEBAX, the middle layer is a network braided by stainless steel wires, and the inner layer is polytetrafluoroethylene (PTFE). Alternatively, the outer cannula 200 is adhered to the stress dispersion tube 700 that is adhered to the guide tube. Additionally, the part of the channel of the joint member 600 for receiving the guide tube has an inner diameter greater than that of the part for receiving the stress dispersion tube 700.

FIG. 10 shows that the stiffness progressively increases from left to right. Particularly, the outer cannula 200 is the tube braided by PEBAX steel wires at the first stage. The outer cannula 200 is sleeved by PA12 to increase hardness at the second stage. The tuber head is sleeved to increase hardness at the third stage. The guide tube (i.e. three-way tube 500) is formed from ABS material at the fourth stage. In addition, the outer cannula is adhered to the stress dispersion tube, which is attached to the three-way tube. The rubber head is sleeved on the joint site of these three elements, and forms a stress dispersion structure with four-stage gradient harness. The stress dispersion structure of the four-stage gradient hardness increases the flexibility of the tube and ensures that the tube will not be easily broken off.

The above is an example of the stress dispersion assembly for the present invention. Other suitable materials known can be used and for the connection of respective elements.

The method for manufacturing the vascular stent delivery system is described below in detail.

The method for manufacturing the vascular stent delivery system includes, but is not limited to, providing a housing, an outer cannula, an inner cannula, and a driving assembly. The outer cannula is configured to be disposed outside of the housing and coupled to it through the stress dispersion assembly. The stress dispersion assembly is used for dissipating the stress concentrated at the joint of the outer cannula and housing. The inner cannula is partly contained within the housing and one end of it extends into the outer cannula. The driving assembly is connected within the housing and operably engaged with a part of the inner cannula disposed within the housing. This part exists to axially move the outer cannula.

The stress dispersion assembly can be configured as the elements in the third embodiment.

In yet another example, the guide tube is configured as a three-way tube similar to the LUER tube. This tube has a first end extending into the joint member, a second end disposed within the housing and in communication with the first end, and a third end disposed between the first and second ends extending out from the outer space housing. The inner cannula is inserted into the second end of the three-way and passes through the three-way tube to extend from the first end of the three-way tube into the outer cannula. An opening is present at the end of the three-way tube and a joint cap is available to close this opening in order to prevent fluid, such as blood, from flowing out. Upon completing transportation of the vascular stent, the joint cap can be opened and the cleaning fluid can be added to clean the front portion of the vascular stent delivery system.

A sealing assembly can be disposed at the distal end of the three-way tube's second end through which the inner cannula passes. This assembly may include an O-shaped ring and a cover platen for fixing this ring. The O-shaped ring is also configured to have thickness gradually decreased from the center to the edge. In other words, the surface for contacting the O-shaped ring with the inner cannula is coated with a lubricating layer.

The vascular stent delivery system manufactured by the above method allows the tube to maintain flexibility and protects it from being broken off. Meanwhile, the operability and service life of this system can be effectively improved.

Example 3

The vascular stent delivery system may comprise of, but is not limited to, a housing consisting of a right half 110, a left half 120, a cleaning tube 200, an outer cannula 200, an inner cannula 800, and a driving assembly 400.

The specific structure of the vascular stent delivery system, such as the outer cannula 200, the inner cannula 800, the driving assembly 400, the three-way tube 500, and cleaning tube 300 are described as the above examples. As an alternative, the cleaning tube 300 can be omitted. For the disposable vascular stent delivery system, there is no need to clean the delivery system by using the cleaning tube 300. Alternatively, in other embodiments described herein, the three-way tube 500 can be omitted. For the disposable vascular stent delivery system, there is no need to use the three-way tube 500 to clean. Therefore, such vascular stent delivery system does not comprise the three-way tube 500. As such, the first end of the inner cannula 800 is directly inserted into the outer cannula 200.

Figure 11:
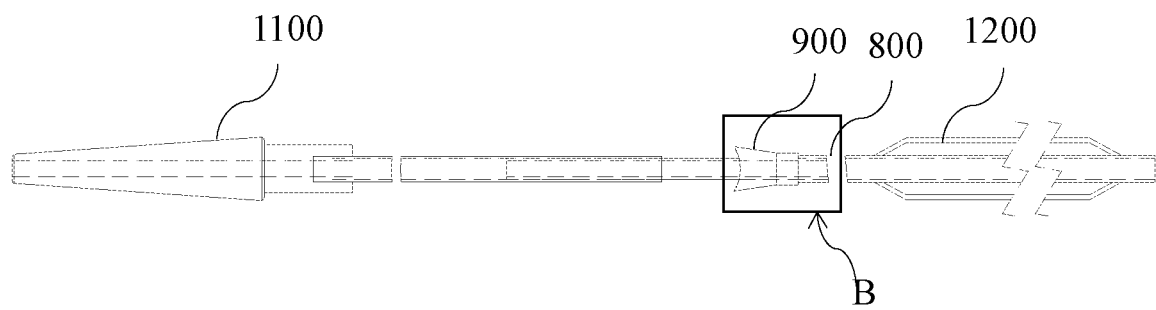
FIG. 11 is a schematic view of one exemplary inner cannula.

In the present example, at least a part of the inner cannula 800 is connected to the outer cannula 200. FIG. 11 shows one end of the inner cannula 800 coupled to the conical tip (TIP) 1100 and another end passing through the inner cannula 1200. The TIP 1100 is disposed at the end of the outer cannula 200 for introducing the tubing assembly to move in the vessels. The inner cannula 1200 is used to maintain the inner cannula 800 to axially move in the outer cannula 200 for preventing the inner cannula 800 from bending in the outer cannula 200. Rachets 900 are connected to the inner cannula 800. Particularly, the rachets 900 are disposed on the region for equipping the vascular stent on the inner cannula 800 (i.e. between the inner cannula 1200 and the TIP 1100). The rachets 900 can be formed from the elastic materials such as nickel-titanium allow and are configured to move the vascular stent to the lesion site where the inner cannula 800 moves relative to the outer cannula 200. Specifically, when the rachets 900 reach the outer cannula 200, the inner cannula 800 is pushed forward and the rachets 900 catch the inner wall of the vascular stent to release the vascular stent to the lesion site. Meanwhile, the rachets 900 extend out of the outer cannula 200. The inner cannula 800 is pushed back such that the rachets 900 move back into the outer cannula 200 catching a segment of the vascular stent's inner wall to push the segment out. This action is repeated until the stent is completely released. Therefore, the inner cannula can be adapted for the vascular stent with different length or various lesion sites to improve compatibility, simplify the operation, and reduce the overall cost of the delivery system.

Figure 12:
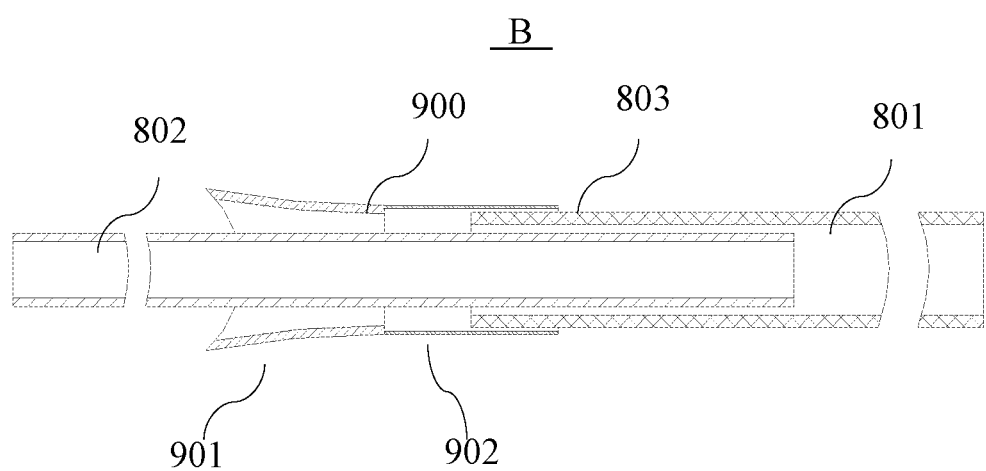
FIG. 12 is an enlarged view of part B of FIG. 11.
Figure 13:
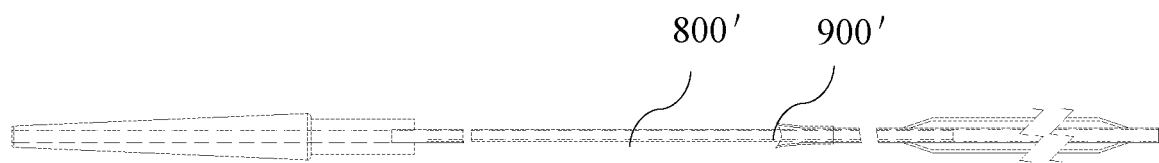
FIG. 13 shows the delivery system's inner cannula for vascular stent in the prior arts.

FIG. 12 shows the inner cannula 800 may comprise of a metal braided tube 801, a metal tube 802 coupled to the metal braided tube 801, a connection tube 803 sleeved on the joint of the metal tube 802 and the metal braided tube 801. The connection tube 803 is adhered to the metal braided tube 801 and the metal tube 802 by adhesive (e.g. anaerobic adhesive). The metal tube 802 is coupled to TIP and the metal braided tube 801 is coupled to a part (e.g. other metal tube) of the inner cannula 800, which is coupled to the driving assembly 400. In yet another assembly, the metal tube 802 can be a nickel-titanium tube. For instance, a part of the metal tube 802 coupled to the connection tube 803 can have a spiral-cutting groove (not shown) along the longitudinal length of the metal tube. When the metal tube 802 adheres to the connection tube 803, the adhesive goes into the spiral-cutting groove to enhance the adhering strength. Meanwhile, when the inner cannula 800 enters the bending lesion site, the passability is improved.

FIG. 12 shows that the rachets 900 are connected to the metal tube 802 and are adjacent to or coupled to the connection tube 803. The outer surface of the rachets 900 and connection tube 803 are linked together with smooth transition. As such, the number of stairs on the outer surface of the inner cannula can be reduced and the adverse influence on transportation and operation of the vascular stent is decreased. In another embodiment, the rachets 900 have a sharp corner 901 and base 902. The sharp corner 901 radially expands outward from the base 902 along the axial direction of the metal tube 802. In other words, the sharp corner 901 radially expands along the axis of the metal tube 802 as the centerline such that the linear distance between the respective peaks of two sharp corners 902 is greater than the radial size of the base 902. The diameter of the base 902 is equivalent to the diameter of the connection tube 803. Alternatively, the rachets 900 can be formed from the elastic materials such as shape memory alloy and is coupled to the metal tube of the inner cannula 800 by laser welding. Therefore, the rigidity of the location on which the rachets are disposed is enhanced and the bending phenomenon from a lack of rigidity in the prior arts can be addressed.

In yet another embodiment, the metal braided tube 801 has a three-layer structure in which the inner polytetrafluoroethylene (PTFE) layer, the outer PEBAX (block polyether acidamide resin) layer and the middle layer between the inner and outer layer is a layer braided by metal wires such as a network braided by the stainless-steel wires. The metal tube 802 is fixably coupled to the metal braided tube 801, including welding the metal tube 802 to the layer braided by the metal wires in the metal braided tube 801 (i.e. laser welding the nickel-titanium tube to the layer braided by the metal wires).

In yet another version, the connection tube 803 can be omitted. The inner cannula consists of the metal braided tube and the metal tube. One end of the metal tube is coupled to the metal braided tube and the other end is coupled to TIP. One end of the metal braided tube is coupled to the metal tube and the other end passes through the inner cannula. One end of the metal tube is inserted into the other and is fixably coupled to it.

Under the circumstance that the inner cannula is made of the metal braided tube, the nickel-titanium tube, the connection tube, the connection tube with ultrathin wall is used without affecting the connection strength among the elements in case of controlling the wall thickness. The metal tube with ground ultrathin wall, having a thickness of 0.02 mm, is used at the front end of the inner cannula for connection, which cannot be achieved by other polymer plastic tube. The connection method includes inserting the nickel-titanium tube into the metal braided tube, sleeving the connection tube on each half of these two tubes, coating the anaerobic adhesive on the inner wall of the connection tube and welding the nickel-titanium tube to the metal braided tube by laser welding. Such method can effectively control the wall thickness of the connection tube's inner wall. When the inner cannula is repeatedly pushed, scratching the stent by the connection tube's head has influence on the pushing effect, which can be avoided. Even if the anaerobic adhesive drops off or faulty welding occurs, it can be insured that the TIP of the inner cannula will not drop into the body and medical accident can be avoided.

One elastic nickel-titanium rachet is added to the inner cannula's metal tube. When this rachet is within the outer cannula, the elastic nickel-titanium rachet catches the stent's inner wall to release it out of the lesion site's outer cannula. The bard is pulled back into the outer cannula and catches one segment's inner wall to push it outward. This action is repeated until the stent is completely released.

The rachet is expanded as a bellmouth with sharp corner using nickel-titanium cutting thermoforming process. For 6F sheath (i.e. the outer cannula with diameter of 6F), the linear distance between the two sharp corners is greater than 1.35 mm. The inner cannula is designed to have a uniform size so that it can push the vascular stent into a 6F sheath. This addresses the problem in the prior delivery system that it needs to tailor the inner cannula's length according to the stent's length and diameter. The vascular stent can be repeatedly pushed through the delivery system's hand operation via short distance and has good maneuverability.

Example 4

The vascular stent delivery system may consist of a right half housing 110, a left half housing 120, a cleaning tube 300, a tubing assembly with an outer cannula 200, an inner cannula 800, and a driving assembly 400.

Specific structures of the vascular stent delivery system such as the outer cannula 200, the inner cannula 800, the driving assembly 400, the three-way tube 500, and the cleaning tube 300 are described as the above example. Alternatively, in other embodiments as described herein, the cleaning tube 300 can be omitted. For example, there is no need to clean the vascular stent delivery system using the cleaning tube 300 for the disposable system. Alternatively, in other versions, the three-way tube 500 can be omitted. For instance, for the vascular stent delivery system, there is no need to clean the delivery system using the three-way tube 500. Therefore, such vascular stent delivery system does not comprise the three-way tube 500. As such, the first end of the inner cannula 800 is directly inserted into the outer cannula 200.

Figure 14:
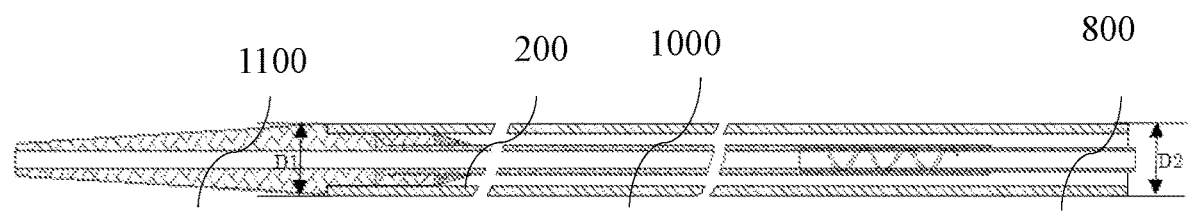
FIG. 14 is a cross-sectional view of one exemplary tubing assembly.

FIG. 14 shows the tubing assembly used for the vascular stent delivery system. It is made of an outer cannula 200 and an inner cannula 800 axially passing through the outer cannula 200 and a tip 1100 having a channel passing through it along the longitudinal direction. A part of this tip is inserted into the outer cannula 200 and coupled to and in communication with the inner cannula 500 through a connection tube 1000 for introducing the movement of the outer cannula 200 and the inner cannula 800 in the vessels. The connection tube 1000 is formed through the injection molding method in the channel of the tip 1100.

Figure 15:
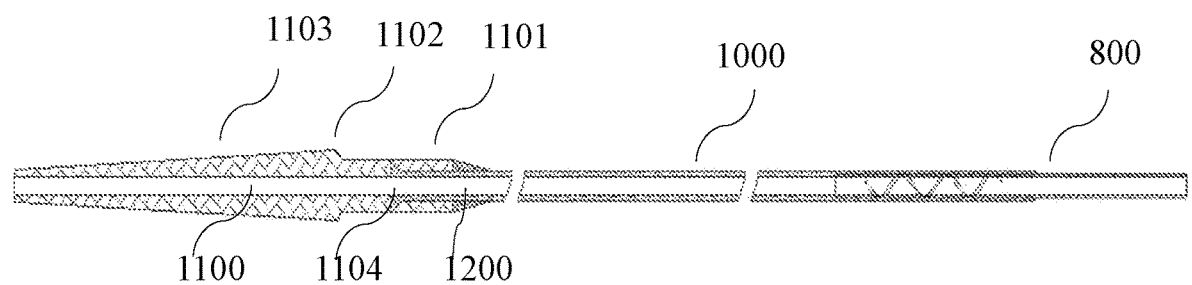
FIG. 15 is a cross-sectional view of the inner cannula and tip of the tubing assembly.

The tubing assembly is described below in detail by referring FIG. 14 in combination with FIG. 15. The outer cannula is omitted in FIG. 15 and the inner cannula 800 and tip 1100 are shown in FIG. 15. In this embodiment, the tip 1100 may comprise of a joint part, a stopping part, and a guide part. The joint part 1101 for the inner cannula is inserted into the outer cannula 200 and coupled to a part of the inner cannula 800 disposed within the outer cannula 200 via the connection tube 1000. A stopping part 1102 is coupled to the joint part 1101 for the inner cannula and forms a stair structure together with the joint part 1101 for the inner cannula, making contact with the end of the outer cannula 200 and having a diameter equivalent to the diameter of the outer cannula (i.e. D1=D2). A guide part 1103 disposed at a side opposite to the joint part 1101 for inner cannula and coupled to the stopping part 1102 for the outer cannula has a diameter gradually and linearly decreasing from the stopping part of the outer cannula (i.e. the diameter of the guide part 1103 is proportionally or linearly decreased from the stopping part 102 for the outer cannula along the axial length direction). The cross-section of the guide part 1103 is formed as a cone and, thus, the tip 1100 is also referred to as TIP.

The connection tube 1000 is a plastic tube formed in the tip 1100 by injection molding. The engaging intensity among the tip, the connection tube, and the inner cannula is increased by coupling the connection tube through injection molding to the inner cannula, such that the tip is prevented from accidentally dropping into the body, and the reliability of the vascular stent delivery system is enhanced. In one embodiment described herein, a recess 1104 is incorporated into the joint part 1101 of the channel's inner wall for the inner cannula. A part of the connection tube 1000 is formed in the joint part 1101 channel of the inner cannula through the injection molding method. Other part of the connection tube 1000 is formed outside the TIP through use of the corresponsive mould and is linked together with the part formed in the channel of the joint part 1101 for the inner cannula. Both parts can be formed by the injection molding at the same time. The inner cannula 800 is inserted into the connection tube 1000. In other words, the end via which the plastic tube is inserted into the tip 1100 has a bellmouth profile, integrally formed through the injection pre-embedded molding such that the engaging intensity between the plastic tube and the tip is enhanced. The outer wall of the inner cannula is adherent to the connection tube's inner wall via adhesives. In the embodiments described herein, the cross-sectional view of the tip 1100, the recess 1104 has a wedge shape, but the present invention is not limited to this. The recess may have other cross-sectional shapes, such as square, cone, and other irregular shapes and the number of the recess is not limited as long as it facilitates increase of the engaging intensity between the plastic tube and the tip.

A structural glue 1200 is connected at the stairs formed by the end of the joint part 1101 for the inner cannula and the outer surface of the connection tube 1000 such that the structural glue 1200 has a size gradually decreasing from the joint part 1101 for inner cannula to the connection tube 1000. It should be noted that the embodiments described here are not limited to this because such structural glue with gradient structure can be omitted or the stairs can be flattened via other materials. When operating by the physicians, the joint part for the TIP's inner cannula can be easily inserted into the outer cannula without "stair and stuck" phenomenon to facilitate device operation.

Alternatively, the connection tube 1000 can be formed in the TIP via injection molding such that the external forming process can be omitted to enhance production efficiency.

Figure 16:
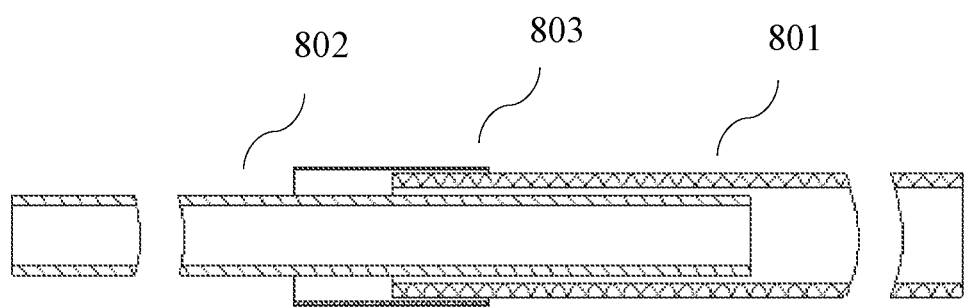
FIG. 16 is an enlarged cross-sectional view of one exemplary inner cannula.

FIG. 16 shows the inner cannula 800 may comprise of a metal braided tube 801, a metal tube 802 coupled to the metal braided tube 801, a connection tube 803 sleeved on the joint of the metal tube 802 and the metal braided tube 801. The connection tube 803 is adhered to the metal braided tube 801 and the metal tube 802 by adhesive (e.g. anaerobic adhesive). The metal tube 802 is inserted into the connection tube 1000 and the metal braided tube 801 is coupled to a part (not individually shown) of the inner cannula that is engaged with the driving assembly 400, which can be a rigid tube, such as a stainless steel tube. In one embodiment, the metal tube 802 can be a nickel-titanium tube. For instance, a part of the metal tube 802 coupled to the connection tube 1000 has a spiral-cutting groove (shown in FIG. 14) along the length direction of the metal tube. When the metal tube is adhered to the plastic tube, the adhesive goes into the spiral-cutting groove to enhance the adhering strength. Meanwhile, when the inner cannula 800 goes into the bending lesion site, the passability can be improved. Alternatively, it is not limited that the part of the metal tube 802 that is coupled to the connection 1000 has a spiral-cutting groove along the direction of the metal tube. Other part of the metal tube 802 can have a spiral-cutting groove to further improve the passability of the metal tube 802.

The metal braided tube has a three-layer structure with a polytetrafluoroethylene (PTFE) inner layer, a block polyether acidamide resin (PEBAX) outer layer, and a metal wire braided middle layer. The metal tube 802 is fixably coupled to the metal braided tube 801, including welding the metal tube 802 to the layer braided by the metal wire in the metal braided tube 801 (i.e. laser welding the nickel-titanium tube to the layer braided by the metal wire).

In yet another version, the connection tube 803 can be omitted. The inner cannula consists of the metal braided tube and the metal tube, one end of which is coupled to the metal braided tube and the other end is coupled to TIP. One end of the metal tube is inserted into one end of the metal braided tube and the metal tube is fixably coupled to the metal braided tube.

Figure 17:
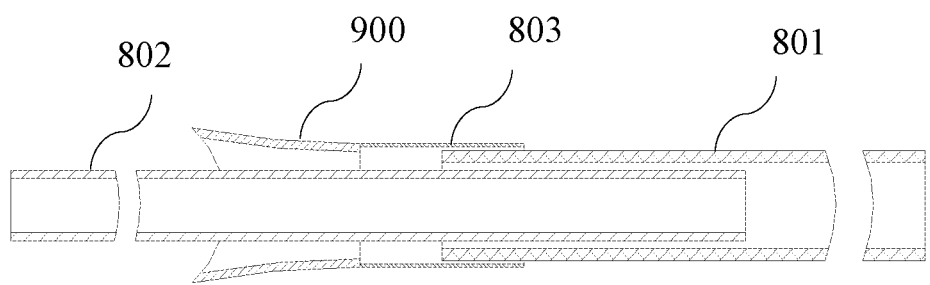
FIG. 17 is an enlarged cross-sectional view of yet another exemplary inner cannula.

FIG. 17 shows yet another embodiment where the tubing assembly is fitted with rachets 900 connected within the metal tube 802. For example, the sharp corner of each of the rachets 900 is radially expanded to the inner cannula and the base of the rachets 900 is coupled to the connection tube 803. The radial size of the base is equivalent to the radial size of the connection tube 803 such that the rachets 900 and outer surface of the connection tube 803 forms a continuous surface to reduce the stairs on the inner cannula's outer surface to facilitate device operation. Meanwhile, the rachets 900 are located within the metal tube to increase rigidity of the site so as to address the bending phenomenon due to a lack of rigidity in the prior arts.

The tip is connected to the inner cannula through the connection member to enhance the engaging intensity so as to prevent the tip from accidentally dropping into the body. This enhances the reliability of the vascular stent delivery system to decrease the overall risk of the operation.

What is claimed is:

1. A vascular stent delivery system, comprising:
    a housing;
    an outer cannula, disposed outside of the housing and coupled to a first end of the housing;
    a cleaning tube, coupled to a second end of the housing, a first end of the cleaning tube is disposed within the housing and a second end of the cleaning tube extends out from the housing;
    an inner cannula, a part of the inner cannula is disposed within the housing, and a first end of the inner cannula is inserted into the outer cannula, and a second end of the inner cannula extends into a cavity of the cleaning tube from the first end of the cleaning tube;
    a driving assembly, a part of the driving assembly is disposed within the housing and operably engaged with a part of the inner cannula disposed within the housing, the driving assembly is configured to drive the inner cannula to axially move in the outer cannula and the cleaning tube; and
    wherein, an end of the second end of the inner cannula is configured to prevent the end of the second end of the inner cannula from scratching the inner wall of the cleaning tube.

2. The vascular stent delivery system of claim 1, wherein configuration of the end of the second end of the inner cannula to prevent the end of the second end of the inner cannula from scratching the inner wall of the cleaning tube comprises forming the end of the second end of the inner cannula as a smooth end surface.

3. The vascular stent delivery system of claim 1, wherein configuration of the end of the second end of the inner cannula to prevent the said end from scratching the inner wall of the cleaning tube comprises inserting the end of the second end of the inner cannula into a heat shrink tube.

4. The vascular stent delivery system of claim 3, wherein a part of the second end of the inner cannula contacted with the heat shrink tube is subject to anti-slipping treatment.

5. The vascular stent delivery system of claim 3, wherein the end of the second end of the inner cannula is fixably coupled to the heat shrink tube.

6. The vascular stent delivery system of claim 1, wherein the cleaning tube is a two-way tube formed integrally.

7. The vascular stent delivery system of claim 6, wherein a fitting for guide wire to pass therethrough is disposed within the cleaning tube and between the first end and the second end of the cleaning tube.

8. The vascular stent delivery system of claim 7, wherein the cavity of the fitting for guide wire to pass therethrough for the cleaning tube comprises an inner diameter, and the inner diameter is gradually decreased.

9. The vascular stent delivery system of claim 6, wherein an opening and a joint cap for closing the opening are disposed at an end of the second end of the cleaning tube.

10. The vascular stent delivery system of claim 6, further comprising:
a three-way tube, the three-way tube is disposed on the first end of the housing, having a first end extending out from the housing to outer space, a second end disposed within the housing and in linear communication with the first end of the three-way tube, and a third end disposed between the first end of the three-way tube and the second end of the three-way tube and extending out from the housing to the outer space; and
wherein the first end of the three-way tube is in communication with the outer cannula, the first end of the inner cannula is inserted into the second end of the three-way tube and passes through the three-way tube, and extends into the outer cannula from the first end of the three-way tube.

11. The vascular stent delivery system of claim 10, wherein an opening and a joint cap for closing the opening are disposed at an end of the third end of the three-way tube.

12. The vascular stent delivery system of claim 10, wherein a sealing assembly is disposed at the end of at least one of the first end of the cleaning tube and the second end of the three-way tube, and the inner cannula passes through the sealing assembly.

13. The vascular stent delivery system of claim 12, wherein the sealing assembly comprises an O-shaped ring and a cover plate for fixing the O-shaped ring.

14. The vascular stent delivery system of claim 13, wherein the O-shaped ring has a thickness gradually decreased from center to edge.

15. The vascular stent delivery system of claim 13, wherein the surface for contacting the O-shaped ring with the inner cannula comprises a lubricating layer.

16. The vascular stent delivery system of claim 15, wherein the lubricating layer comprises any one of parylene, polytetrafluoroethylene, polyvinylpyrrolidone and silicone oil.

* * * * *